(12) United States Patent
Anderson et al.

(10) Patent No.: US 10,792,428 B2
(45) Date of Patent: Oct. 6, 2020

(54) MEDICAMENT DELIVERY DEVICE HAVING GAS PROPELLANT

(71) Applicant: Consort Medical PLC, Hemel Hempstead (GB)

(72) Inventors: Ian Anderson, Cambridgeshire (GB); Alastair Willoughby, Cambridgeshire (GB); Rachel Koppelman, Cambridgeshire (GB)

(73) Assignee: Consort Medical PLC, Hemel Hempstead (GB)

( * ) Notice: Subject to any disclaimer, the term of this patent is extended or adjusted under 35 U.S.C. 154(b) by 348 days.

(21) Appl. No.: 15/567,882

(22) PCT Filed: Apr. 21, 2016

(86) PCT No.: PCT/GB2016/051115
§ 371 (c)(1),
(2) Date: Oct. 19, 2017

(87) PCT Pub. No.: WO2016/170347
PCT Pub. Date: Oct. 27, 2016

(65) Prior Publication Data
US 2018/0104416 A1    Apr. 19, 2018

(30) Foreign Application Priority Data
Apr. 21, 2015 (GB) .................................. 1506789.5

(51) Int. Cl.
*A61M 5/20* (2006.01)
*A61M 5/32* (2006.01)

(52) U.S. Cl.
CPC .......... *A61M 5/2046* (2013.01); *A61M 5/326* (2013.01); *A61M 2005/206* (2013.01);
(Continued)

(58) Field of Classification Search
CPC .... A61M 5/2046; A61M 5/2053; A61M 5/30; A61M 5/326; A61M 2005/2013; A61M 2005/206; A61M 2205/8218; F15B 15/19
See application file for complete search history.

(56) References Cited

U.S. PATENT DOCUMENTS 2,960,087 A    11/1960  Uytenbogaart
4,031,889 A     6/1977  Pike
(Continued)

FOREIGN PATENT DOCUMENTS

CN    1909939 A    2/2007
EP    2438945 A1   4/2012
(Continued)

OTHER PUBLICATIONS

International Search Report and Written Opinion dated Jul. 28, 2016, for corresponding International Application No. PCT/GB2016/051115; International Filing Date: Apr. 21, 2016 consisting of 14-pages.
(Continued)

*Primary Examiner* — Tiffany Legette
(74) *Attorney, Agent, or Firm* — Christopher & Weisberg, P.A.

(57) ABSTRACT

A medicament delivery device (10) comprising a syringe (12) having a barrel with an open end, and an axially moveable stopper (18) received in the barrel separating a first chamber axially forwards of the stopper from a second chamber axially rearwards of the stopper. The medicament delivery device further including an expandable drive housing (24) arranged to receive a propellant from a propellant source (36) for providing a vapour pressure, the expandable drive housing having a narrow channel in fluid communication with the second chamber. The expandable drive housing is expandable upon receiving propellant from the propellant source and, upon expansion, causes forward axial
(Continued)

movement of the syringe. Propellant introduced into the expandable housing may pass through the narrow channel into the second chamber and cause forward axial movement of the stopper in the barrel to expel medicament contained in the first chamber through the open end, where axial movement of the stopper in the barrel commences after axial movement of the syringe.

20 Claims, 6 Drawing Sheets

(52) U.S. Cl.
CPC .............. *A61M 2005/2013* (2013.01); *A61M 2205/8218* (2013.01)

(56) References Cited

U.S. PATENT DOCUMENTS

| | | | |
|---|---|---|---|
| 2003/0233070 | A1 | 12/2003 | De La Serna et al. |
| 2004/0015125 | A1* | 1/2004 | Alexandre .............. A61M 5/30 604/69 |
| 2006/0269484 | A1* | 11/2006 | Knopeck ................ A61K 31/44 424/45 |
| 2013/0237951 | A1* | 9/2013 | Oda ........................ A61M 5/46 604/500 |
| 2014/0114248 | A1 | 4/2014 | DeSalvo et al. |

FOREIGN PATENT DOCUMENTS

| | | |
|---|---|---|
| JP | 2013151503 A | 8/2013 |
| WO | 2005070481 A1 | 8/2005 |
| WO | 2013182858 A1 | 12/2013 |
| WO | WO-2013182861 A1 * 12/2013 | .............. A61M 5/44 |
| WO | 2014081746 A1 | 5/2014 |

OTHER PUBLICATIONS

UKIPO Search Report and Written Opinion dated Oct. 27, 2015, for corresponding International Application No. GB1506789.5; International Filing Date: Apr. 21, 2015 consisting of 3-pages.

Office Action dated Nov. 14, 2019, for corresponding Chinese Application No. 201680023154.X, consisting of 7-pages.

Japanese Office Action dated Feb. 13, 2020, for corresponding Japanese Application No. 2017-555365, consisting of 11-pages.

* cited by examiner

MEDICAMENT DELIVERY DEVICE HAVING GAS PROPELLANT

CROSS-REFERENCE TO RELATED APPLICATIONS

This application is a Submission under 35 U.S.C. § 371 for U.S. National Stage Patent Application of, and claims priority to, International Application Number PCT/GB2016/051115 entitled MEDICAMENT DELIVERY DEVICE HAVING GAS PROPELLANT, filed Apr. 21, 2016, which is related to and claims priority to Great Britain Patent Number 1506789.5, filed Apr. 21, 2015, the entirety of all of which are incorporated herein by reference.

The present invention relates a medicament delivery device, and in particular, to a medicament delivery device that is powered by a propellant.

BACKGROUND

Medicament delivery devices such as autoinjectors are known. Known autoinjector devices are capable of automatically performing multiple actions including, for example, penetrating an injection site with a needle and expelling medicament through the needle. In many situations, it is desirable for the needle to be fully inserted in the injection site to the required penetration depth before expulsion of the medicament begins. This is particularly desirable in devices where the penetration of the needle is automated.

WO2005/070481 (The Medical House Plc) describes an example of a known autoinjector device in which the sequence of automatic penetration and injection stages is controlled by a single component. In particular, an inner housing component has flexible tags that are selectively engageable with the syringe and plunger rod to determine a desired sequence.

It is an object of certain embodiments of the present invention to provide an alternative medicament delivery device that is capable of controlling a sequence of distinct actions.

BRIEF SUMMARY OF THE DISCLOSURE

In accordance with an aspect of the present invention there is provided a medicament delivery device comprising:

a syringe having a barrel with an open end, and an axially moveable stopper received in the barrel separating a first chamber axially forwards of the stopper from a second chamber axially rearwards of the stopper;

an expandable drive housing arranged to receive a propellant from a propellant source for providing a vapour pressure, the expandable drive housing having a narrow channel in fluid communication with the second chamber;

wherein the expandable drive housing is expandable upon receiving propellant from the propellant source and, upon expansion, causes forward axial movement of the syringe; and wherein propellant introduced into the expandable housing may pass through the narrow channel into the second chamber and cause forward axial movement of the stopper in the barrel to expel medicament contained in the first chamber through the open end, where axial movement of the stopper in the barrel commences after axial movement of the syringe.

In certain embodiments, the expandable drive housing may comprise a first part that is sealable to the propellant source, and a second part sealed to the barrel, wherein the second part is sealingly telescopically slidable relative to the first part so as to be capable of expanding the expandable drive housing.

The medicament delivery device may further comprise a needle in fluid communication with the open end. The syringe may be moveable from a first axial position in which the needle is not exposed to a second axial position that is axially forwards of the first axial position and in which the needle may penetrate an injection site, the autoinjector being configured such that the syringe is in the second axial position prior to commencement of axial movement of the stopper in the barrel. The medicament delivery device may further comprise an axially moveable needle shield that is moveable between a first shield position in which the needle is exposed when the syringe is in the second axial position and a second shield position in which the needle is not exposed when the syringe is in the second axial position. The needle shield may be biased by biasing means towards the second shield position, where the biasing means may comprise a spring.

The medicament delivery device of may further comprise blocking means that are configured to at least partially restrict a flow rate of propellant through the narrow channel, the blocking means being moveable between a first position and a second position relative to the narrow channel, wherein in the second position the blocking means permits a greater flow rate of propellant through the narrow channel relative to the flow rate of propellant through the narrow channel when the blocking means are in the first position.

The narrow channel may extend radially through the second part. The blocking means may be axially moveable on the second part between the first position and the second position. The blocking means may comprise a circumferential seal disposed on the second part.

The blocking means may further comprise a first abutment part and the medicament delivery device further comprises a second abutment part, wherein the first abutment part is configured to abut the second abutment part as the second part moves axially relative to the first part, and wherein abutment of the first abutment part and the second abutment part causes axial movement of the blocking means from the first position to the second position. The second abutment part may be provided on the first part. In the first position the blocking means may substantially prevent flow of propellant through the narrow channel.

In accordance with another aspect of the present invention, there is provided a medicament delivery device comprising:

a syringe having a barrel with an open end, and an axially moveable stopper received in the barrel separating a first chamber axially forwards of the stopper from a second chamber axially rearwards of the stopper;

an expandable drive housing arranged to receive a propellant from a propellant source for providing a vapour pressure, the expandable drive housing having a channel in fluid communication with the second chamber; and blocking means configured to at least partially restrict a flow rate of propellant through the channel, the blocking means being moveable between a first position and a second position relative to the channel such that in the second position the blocking means permits a greater flow rate of propellant through the channel relative to the flow rate of propellant through the channel when the blocking means are in the first position;

wherein the expandable drive housing is expandable upon receiving propellant from the propellant source and, upon expansion, causes forward axial movement of the syringe and movement of the blocking means from the first position to the second position; and when the blocking means are in the second position propellant introduced into the expandable housing may pass through the channel into the second chamber and cause forward axial movement of the stopper in the barrel to expel medicament contained in the first chamber through the open end, where axial movement of the stopper in the barrel commences after axial movement of the syringe.

The channel may extend radially through the second part. The blocking means may be axially moveable on the second part between the first position and the second position. In certain embodiments, the blocking means may comprise a circumferential seal disposed on the second part. The blocking means may further comprise a first abutment part and the medicament delivery device further comprises a second abutment part, wherein the first abutment part is configured to abut the second abutment part as the second part moves axially relative to the first part, and wherein abutment of the first abutment part and the second abutment part causes axial movement of the blocking means from the first position to the second position. The second abutment part may be provided on the first part.

In the first position the blocking means may substantially prevent flow of propellant through the channel.

In certain embodiments, the expandable drive housing may comprise a first part that is sealable to the propellant source, and a second part sealed to the barrel, wherein the second part is sealingly telescopically slidable relative to the first part so as to be capable of expanding the expandable drive housing.

The medicament delivery device may further comprise a needle in fluid communication with the open end.

The syringe may be moveable from a first axial position in which the needle is not exposed to a second axial position that is axially forwards of the first axial position and in which the needle may penetrate an injection site, the autoinjector being configured such that the syringe is in the second axial position prior to commencement of axial movement of the stopper in the barrel.

The medicament delivery device may further comprise an axially moveable needle shield that is moveable between a first shield position in which the needle is exposed when the syringe is in the second axial position and a second shield position in which the needle is not exposed when the syringe is in the second axial position. The needle shield may be biased by biasing means towards the second shield position. The biasing means may comprise a spring.

In certain embodiments, a time period may elapse between the syringe arriving at the second axial position and the commencement of axial movement of the stopper in the barrel, the time period being at least 0.005, 0.01, 0.05 or 0.1 seconds.

An initial increase in pressure in the second chamber may be at a rate that is less than 50%, 40%, 30%, 20%, 10%, 5% or 1% of a rate of initial increase of pressure in the expandable drive housing.

In certain embodiments, the propellant source may contain a liquefied gas.

In certain embodiments, the propellant source may contain one or more hydrofluoroalkanes ("HFAs"). For example, the propellant source may contain one or more of HFA 134a, HFA227, HFA 422D, HFA 507, or HFA 410A.

In certain embodiments, the propellant source may contain one or more hydrofluoroolefins ("HFOs"). For example, the propellant source may contain one or both of HFO 1234yf or HFO 1234ze.

BRIEF DESCRIPTION OF THE DRAWINGS

Embodiments of the invention are further described hereinafter with reference to the accompanying drawings, in which.

DETAILED DESCRIPTION

Figure 1:
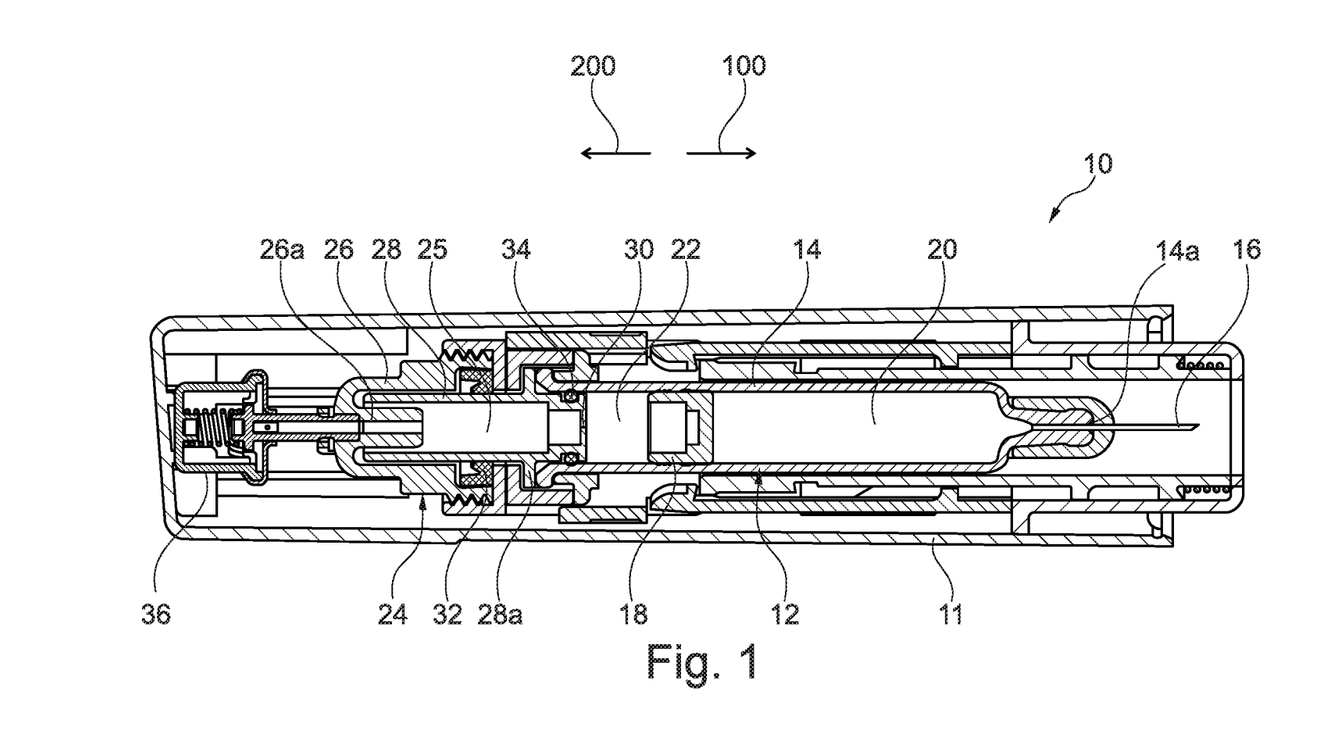
FIG. 1 is a cross-sectional view of an autoinjector prior to use according to an embodiment of the present invention.

FIG. 1 shows a medicament delivery device in the form of an autoinjector 10 according to an embodiment of the present invention. Throughout the specification, references to the forward axial direction are intended to mean towards the front end of the medicament delivery device, i.e. parallel to direction 100 shown in FIG. 1. Conversely, references to the rearward axial direction are intended to mean away from the front end of the medicament delivery device, i.e. parallel to the direction 200 shown in FIG. 1.

The autoinjector 10 has an outer housing 11 that includes a syringe 12 having a barrel 14 and a stopper 18 disposed in and axially moveable within the barrel 14. The stopper 18 separates a first chamber 20 in the barrel 14 from a second chamber 22, where the first chamber 20 is axially forwards of the stopper 18 and the second chamber 22 is axially rearwards of the stopper 18. The first chamber 20 may contain a medicament substance for delivery to a patient. The barrel 14 has a forward open end 14a with a needle 16 attached thereto, where the needle 16 is in fluid communication with the first chamber 20 (and any medicament contained therein) via the open end 14a.

The autoinjector 10 also includes an expandable drive housing 24 for axially moving the syringe 12 within the outer housing 11. In the embodiment shown in the Figures, the expandable drive housing 24 includes a first part 26 and a second part 28 in the form of a moveable piston that is telescopically slidable in the first part 26. Despite being telescopically slidable relative to the first part 26, the second part 28 is sealed to the first part 26 by a sliding seal 32. In particular, the sliding seal 32 permits axial movement of the second part 28 relative to the first part 26 whilst maintaining a fluid-tight seal therebetween. The expandable drive housing 24 defines a drive chamber 25 capable of receiving a propellant from a propellant source 36. In the embodiment shown in the Figures, the first part 26 has a fluid channel 26a that fluidly connects the propellant source 36 to the drive chamber 25.

In any embodiment of the present invention, the propellant may be any suitable propellant for providing a vapour pressure to the drive chamber 25. In certain embodiments, the propellant may be a liquefied gas that vaporises to provide a vapour pressure. In certain embodiments, the propellant may be or contain a hydrofluoroalkane ("HFA"), for example HFA 134a, HFA227, HFA 422D, HFA 507, or HFA 410A. In certain embodiments, the propellant may be or contain a hydrofluoroolefin ("HFO") such as HFO 1234yf or HFO 1234ze.

The second part 28 is sealed to the barrel 14 by a seal 34 and additionally includes a radially projecting flange 28a that extends so as to be axially aligned with a part of the barrel 14. The second part 28 includes a narrow channel 30 that fluidly connects the drive chamber 25 to the second chamber 22 such that propellant received in the drive chamber 25 may pass through the narrow channel 30 into the second chamber 22 and act on the stopper 18.

The autoinjector 10 is shown in a pre-use state in FIG. 1. In particular, the propellant source 36 is in a closed configuration such that no propellant may exit the propellant source and enter the drive chamber 25.

Figure 2:
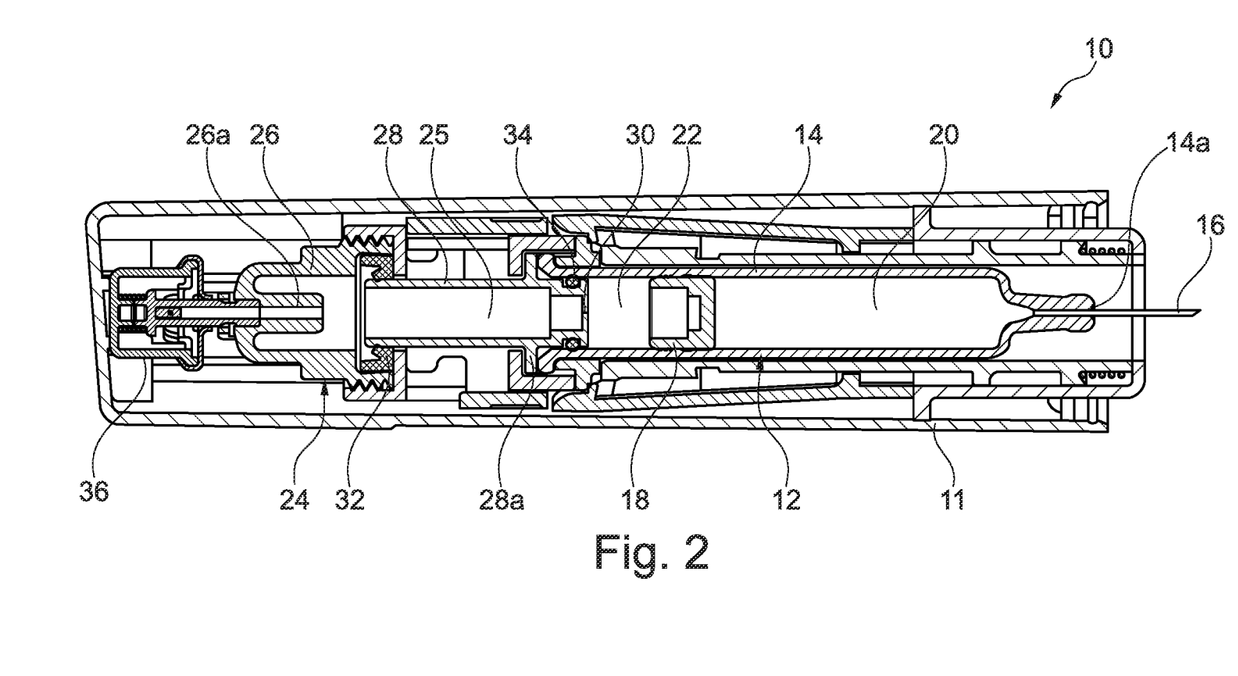
FIG. 2 is a cross-sectional view of the autoinjector of FIG. 1 at the end of a penetration stage but before a delivery stage.

FIG. 2 shows the autoinjector 10 at the end of a penetration stage in which the syringe 12 has moved from a first axial position (as shown in FIG. 1) to a second axial position. The axially advancing syringe 12 causes the needle 16 to move axially forwardly by a suitable amount so that an injection site (such as a patient's tissue) can be penetrated to a desired depth. To initiate axial movement of the syringe 12 so that it may reach the axial position shown in FIG. 2, the propellant source 36 must be actuated so as to move to an open configuration in which propellant may exit the propellant source 36 and enter the drive chamber 25 via the fluid channel 26a. The propellant provides a vapour pressure to the drive chamber 25 which causes the expandable drive housing 24 to expand. In the particular embodiment shown in the Figures, the increasing vapour pressure in the drive chamber 25 causes the second part 28 to slide axially forwardly through the sliding seal 32 relative to the first part 26 so as to increase the volume of the drive chamber 25. Due to engagement between the second part 28 and the syringe 12 (e.g. by way of abutment between the flange 28a and the barrel 14 and/or by way of friction between the seal 34 and the barrel 14), forward axial movement of the second part 28 causes forward axial movement of the syringe 12. The syringe 12 may travel axially forward so as to cause the needle 16 to penetrate an injection site by a desired amount. For example, for sub-cutaneous delivery, the needle 16 may penetrate the patient's tissue to a depth of around 5 to 6 mm. For intra-muscular delivery, the needle 16 may penetrate the patient's tissue to a depth greater than 10 mm. For intra-dermal delivery, the needle 16 may penetrate the patient's tissue to a depth less than 1 mm.

As propellant is introduced into the drive chamber 25, it begins to pass through the narrow channel 30 and enter the second chamber 22. However, due to the flow restriction created by the narrow channel 30, the second chamber 22 will pressurize at a different, slower rate relative to the drive chamber 25. Eventually, the vapour pressure in the second chamber 22 will be sufficient to provide an axially forward force on the stopper 18 that may overcome the "break free" frictional forces between the stopper 18 and the barrel 14, and the fluid resistance provided by any medicament contained in the first chamber 20. When a sufficient vapour pressure is reached in the second chamber 22, the stopper 18 will begin to move axially forwardly. However, as noted above, the second chamber 22 will pressurize at a different, slower rate relative to the drive chamber 25. The rate of pressure increase in the second chamber 22 is at least partly dependent on the relative dead volumes of the second chamber 22 and the drive chamber 25, in addition to the size of the narrow channel 30. In accordance with the present invention, the stopper 18 only begins moving in the barrel 14 after the syringe 12 begins to move axially forwardly. In certain embodiments of the invention, the syringe 12 is in its second position in which the needle 16 is exposed before the pressure in the second chamber 22 is sufficient to cause the stopper 18 to move axially within the barrel 14. In certain embodiments, the second position is the forwardmost possible position of the syringe 12.

Figure 3:
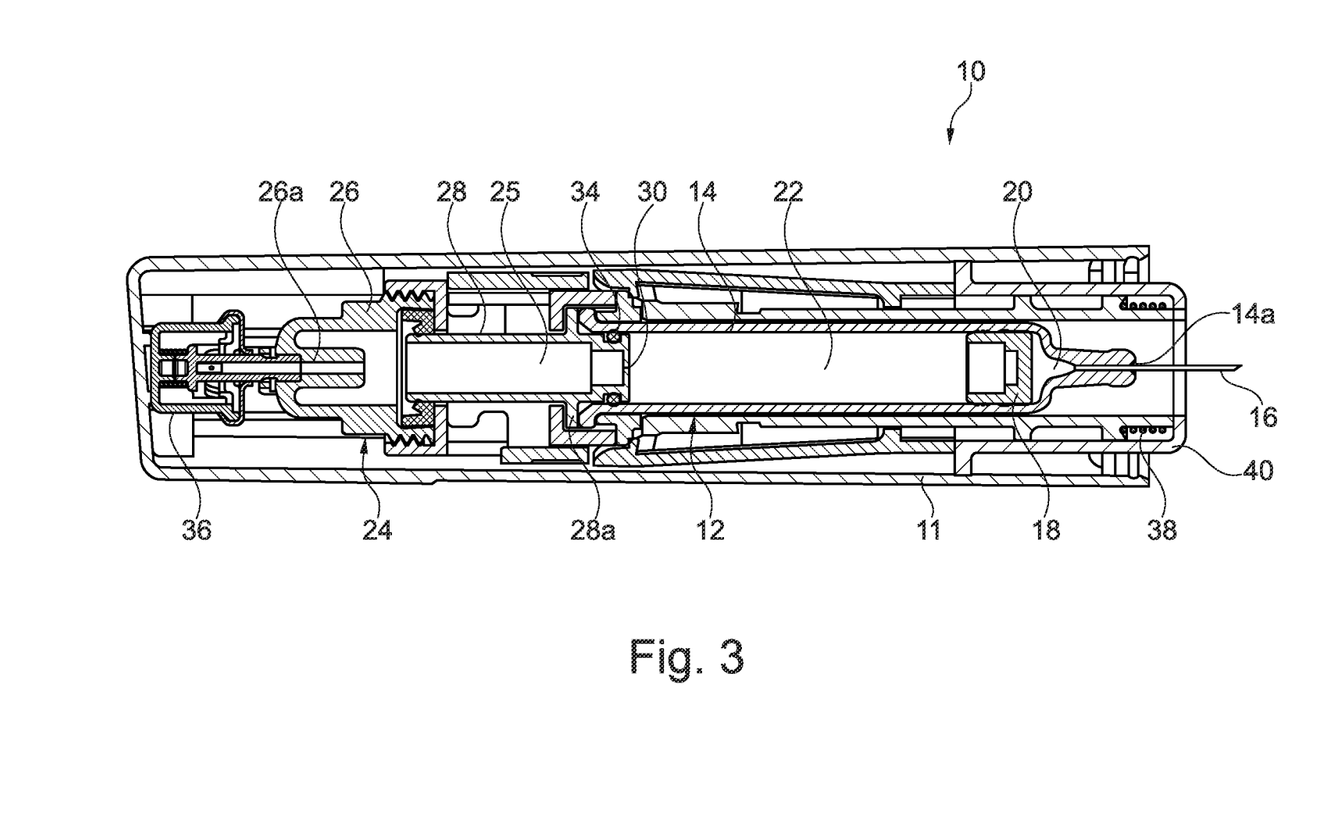
FIG. 3 is a cross-sectional view of the autoinjector of FIG. 1 at the end of a delivery stage.

FIG. 3 shows the autoinjector 10 after an injection stage has been completed in which the stopper 18 has moved axially forwardly to a maximum extent in the barrel 14 in response to increased pressure in the second chamber 22. As such, substantially all of the medicament contained in the first chamber 20 is expelled through the needle 16 to a delivery site.

Figure 4:
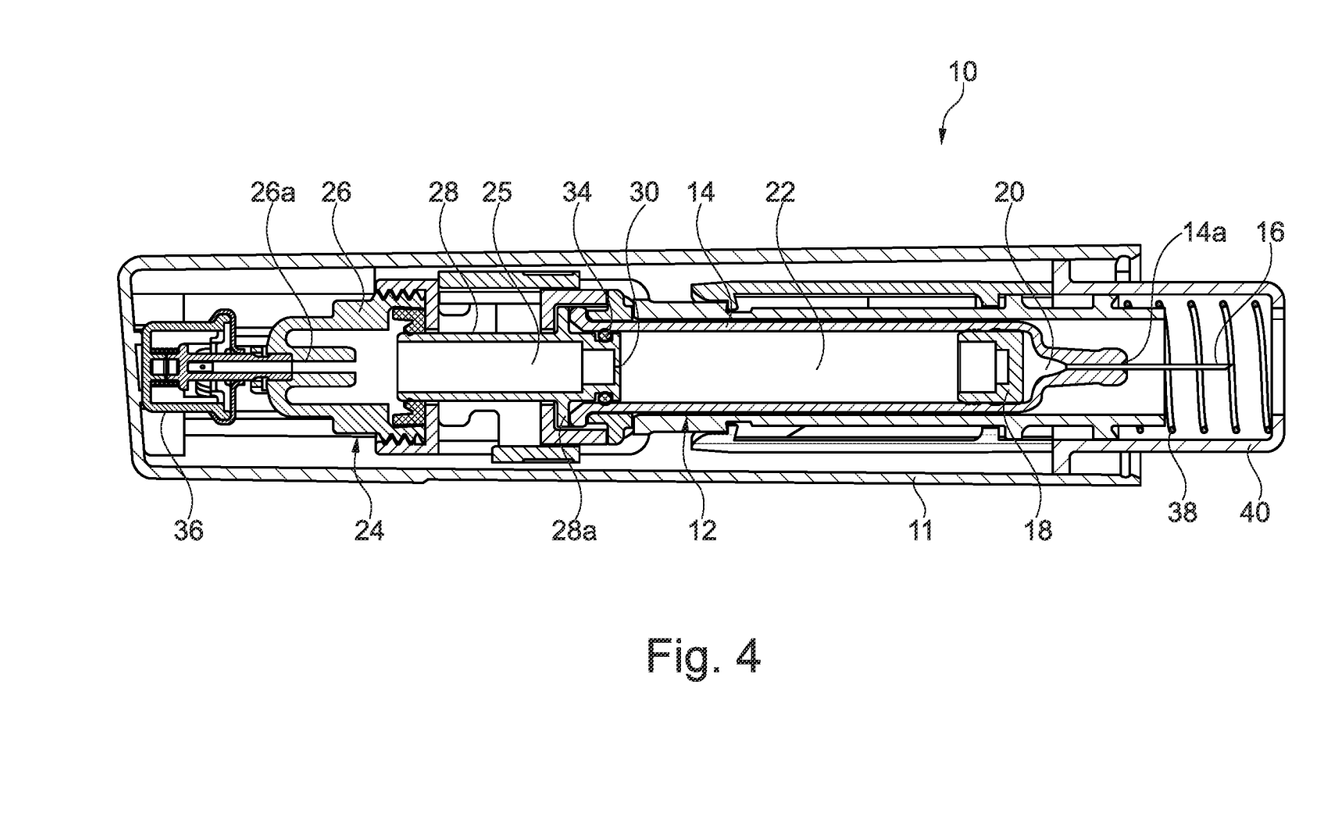
FIG. 4 is a cross-sectional view of the autoinjector of FIG. 1 in which a needle shield is in a needle protecting position.

FIG. 4 shows an embodiment of the autoinjector 10 in a final state subsequent to the state showed in FIG. 3, in which a spring 38 has been allowed to forwardly bias a protective needle shield 40 to a protecting position such that the needle 16 is not exposed. The needle shield 40 may be lockable in the protecting position such that it cannot subsequently be moved to a non-protecting position. In alternative embodiments, any alternative needle shield or needle safety mechanism may be employed to reduce the risk of needle stick injuries after use of the autoinjector. In certain embodiments, no needle shield or needle safety mechanism may be present.

Figure 5:
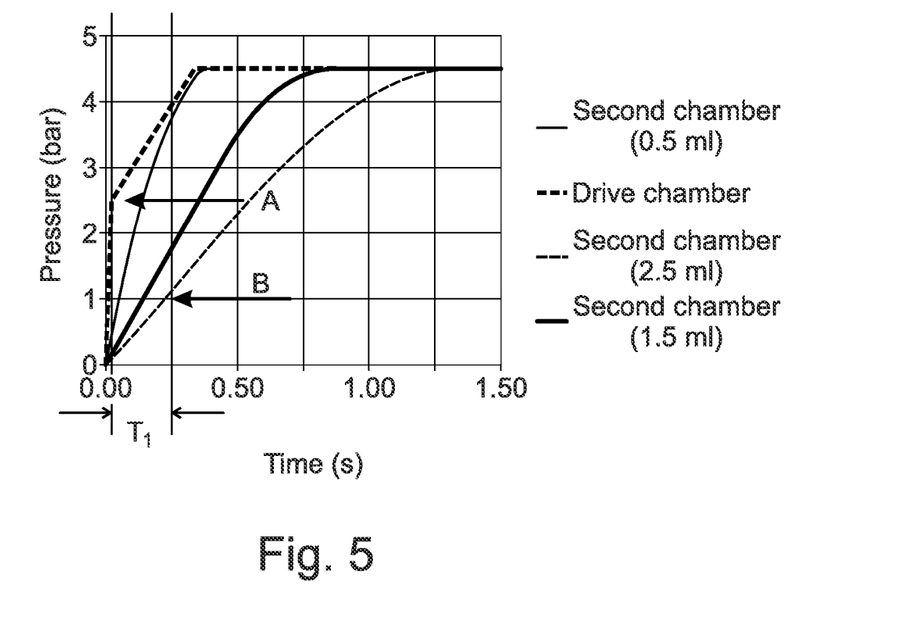
FIG. 5 is a plot of the time dependent pressure profiles of the drive chamber and second chambers of various volumes.

The factors determining the start of delivery (i.e. the initiation of axial movement of the stopper 18 in the barrel 14) are described further below with reference to FIG. 5. FIG. 5 shows example time dependent pressure profiles (as propellant is introduced) of the drive chamber 25 and the second chamber 22 for cases where the second chamber 22 has a dead volume of 0.5 ml, 1.5 ml and 2.5 ml. As is shown in FIG. 5, as propellant is introduced, the pressure in the drive chamber 25 increases rapidly and causes the expandable drive housing 24 to expand and drive the syringe 12 axially forwardly so that the needle 16 penetrates an injection site. At point A indicated on FIG. 5, the syringe 12 and needle 16 have advanced to their maximum forward position such that the insertion or penetration stage is completed. The vapour pressure in the second chamber 22 rises more slowly due to restriction provided by the narrow channel 30. In particular, the mass flow of propellant is driven by the pressure difference between the drive chamber 25 and the second chamber 20, and the size of the narrow channel 30.

Taking the example of a 2.5 ml second chamber 22 where 1 bar of vapour pressure is required to start moving the stopper 18 axially forwards in the barrel 14 (as indicated by point B on FIG. 5), a time period of T1 will elapse between the end of the insertion stage (point A) and the beginning of the delivery stage (point B). It can be seen from FIG. 5 that the vapour pressure rises in the second chamber 22 faster for smaller volumes. Therefore, for a given pressure, the time period T1 will be less for cases where the volume of the second chamber 22 is smaller. In certain embodiments, T1 is at least 0.005, 0.01, 0.05 or 0.1 seconds.

In the examples shown in FIG. 5, the time taken to reach 1 bar after propellant is released from the propellant source 36 is 241 ms for the 2.5 ml second chamber 22, 154 ms for the 1.5 ml second chamber 22, and 62 ms for the 0.5 ml second chamber 22 (note that these time periods are from the initial release of propellant and are not equal to the time period T1 which is from the end of insertion). For comparison, the drive chamber 25 in the example of FIG. 5 reaches 1 bar 13 ms after propellant is released from the propellant source 36. Therefore, the 2.5 ml second chamber 22 takes 228 ms longer than the drive chamber 25 to reach the illustrative pressure of 1 bar, whilst the 1.5 ml second chamber 22 takes 141 ms longer than the drive chamber 25 to reach the illustrative pressure of 1 bar, and the 0.5 ml second chamber 22 takes 49 ms longer than the drive chamber 25 to reach the illustrative pressure of 1 bar. Indeed, in certain embodiments an initial increase in pressure in the second chamber 22 is at a rate that is less than 50%, 40%, 30%, 20%, 10%, 5% or 1% of a rate of initial increase of pressure in the drive chamber 25.

The time between actuating the propellant source 36 and the commencement of delivery (i.e. the movement of the stopper 18 in the barrel 14) or the time between the end of the insertion stage and the commencement of delivery can therefore be controlled by a suitable choice of any one or more of the dead volumes of the drive chamber 25 and the second chamber 22, the dimensions of the narrow channel 30, and the choice of propellant.

Whilst, in the above-described embodiments, the expandable drive housing 24 comprises the first part 26 and the second part 28 where the second part 28 is in the form of a moveable piston, in alternative embodiments any suitable expandable drive housing 24 may be employed. In particular, suitable expandable drive housings 24 are required to define an drive chamber 25 and expand upon receiving propellant from the propellant source 36 so as to drive the syringe 12 axially forwardly. Additionally, suitable expandable drive housings 24 include a narrow channel 30 so as to permit the controlled release of propellant from the drive chamber 25 to the second chamber 22. The expandable drive housing 24 may comprise one or more components and, in certain embodiments, may include expandable features such as bellowed or elastic portions so as to permit expansion.

Whilst, in the above-described embodiments, the barrel 14 has a needle 16 in fluid communication with the open end 14a, in alternative embodiments within the scope of the present invention, the barrel 14 may not include a needle. Indeed, in alternative embodiments, an alternative nozzle or applicator may be affixed or may be connectable to the open end 14a of the barrel. In other embodiments, there may be no further component connected to the open end 14a and medicament may be deliverable directly from the open end. Examples of embodiments not including a needle may include ocular and nasal devices. In embodiments not including needles, the advancement (i.e. forward axial movement) of the syringe may be useful in moving the open end of the barrel (or any component connected thereto) close to the intended delivery site. In the case of a nasal device, for example, the forwardly advancing syringe may cause the open end of the barrel to move further into the nasal cavity towards an intended delivery site.

Figure 6A:
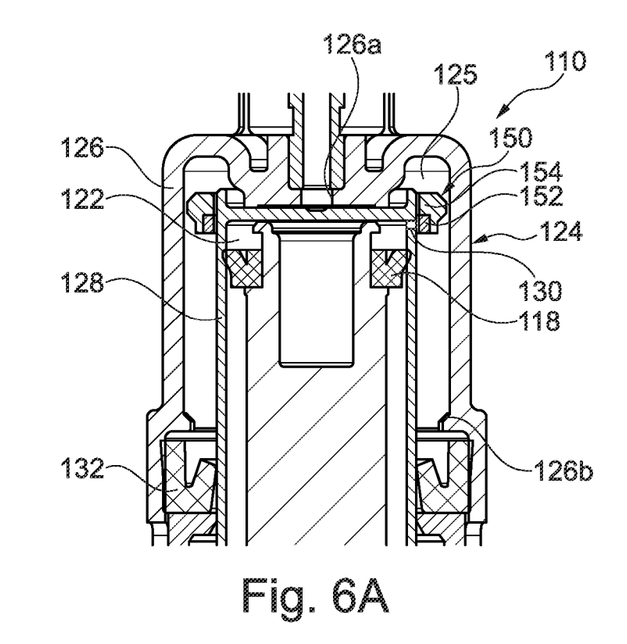
FIGS. 6A and 6B each show a partial cross-sectional view of an autoinjector according to an alternative embodiment of the present invention.
Figure 6B:
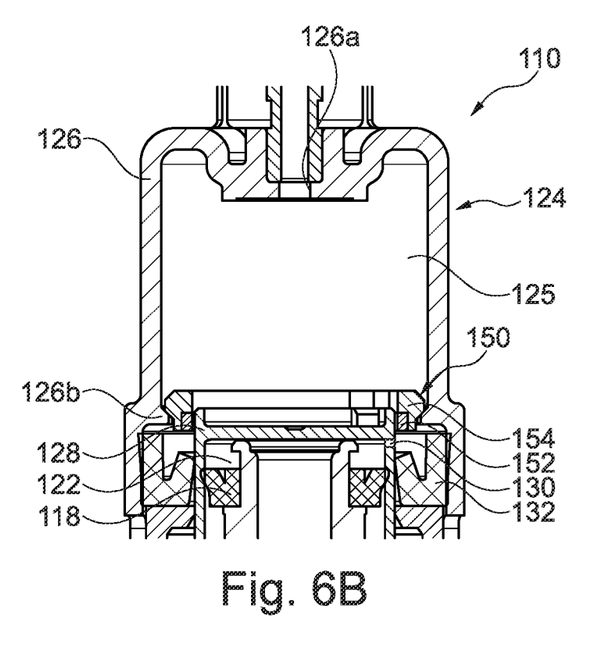

FIGS. 6A and 6B show partial cross-sectional views of a medicament delivery device 110 according to an alternative embodiment of the present invention. The medicament delivery device 110 is an autoinjector and also includes an expandable drive housing 124 for axially moving a syringe (not shown) within a housing (not shown) of the autoinejctor 110. The expandable drive housing includes a first part 126 and a second part 128 in the form of a moveable piston that is telescopically slidable in the first part 126. Despite being telescopically slidable relative to the first part 126, the second part 128 is sealed to the first part 126 by a sliding seal 132. In particular, the sliding seal 132 permits axial movement of the second part 128 relative to the first part 126 whilst maintaining a fluid-tight seal therebetween. The expandable drive housing 124 defines a drive chamber 125 capable of receiving a propellant from a propellant source (not shown). The first part 126 has a fluid channel 126a for fluidly connecting the propellant source to the drive chamber 125. The expandable housing 124 has a connecting channel 130 extending radially through the second part 128 for fluidly connecting the drive chamber 125 to an injection chamber 122 (or "second chamber") that is axially rearward of a stopper assembly 118. The stopper assembly 118 is axially moveable in the second part 128 and a syringe (not shown) to expel a dose of medicament from the syringe.

FIG. 6A shows the autoinjector 110 in a pre-use state in which the connecting channel 130 is blocked by a blocker 150 (or blocking means). The blocker 150 includes a circumferential seal 152 disposed on and around the second part 128, and a collar 154 that is fixed relative to the seal 152 (e.g. by an interference fit and/or adhesive).

When propellant is introduced through the fluid channel 126a into the drive chamber 125 the pressure increases and causes the second part 128 to move axially forwardly relative to the first part 126. In doing so, the second part 128 causes the syringe to move within the housing (e.g. to penetrate an injection site with a needle extending from the syringe). The blocker 150 remains in a first blocking position during this phase and substantially prevents or limits propellant entering the injection chamber 125 so that axial movement of the syringe precedes delivery of medicament.

The first part 126 includes a projection 126b extending radially inwardly from an inner wall. The collar 154 of the blocker 150 forms a first abutment part and the projection 126b forms a second abutment part that abuts the first abutment part when the second part 128 is advanced axially forwardly relative to the first part 126. The abutment between the first abutment part and the second abutment part causes the blocker 150 to move axially on the second part 128 to a second position in which the connecting channel 130 is unblocked or is less occluded by the blocker 150. That is, the seal 152 moves away from the connecting channel 130. As such, propellant (or more propellant than previously) may enter the injection chamber 122 and act on the stopper assembly 118 to cause the delivery of medicament from the syringe. The projection 126b and/or blocker 150 may be circumferentially discontinuous to permit the flow of propellant from the drive chamber 125 to the injection chamber 122. FIG. 6B shows the autoinjector 110 at the end of the penetration phase (i.e. when the expandable drive housing 124 has expanded) but immediately prior to the injection phase (i.e. the blocker 150 is not blocking the connecting channel 130 but the stopper assembly 118 has not commenced movement relative to the second part 128 or syringe).

The connecting channel 130 may or may not be a narrow channel and its size will determine the required size of the blocker 150 required.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A medicament delivery device comprising: a syringe having a barrel with an open end, and a stopper axially moveable and received in the barrel separating a first chamber axially forward the stopper from a second chamber axially rearward the stopper; and an expandable drive housing arranged to receive a propellant from a propellant source for providing a vapour pressure, the expandable drive housing having a narrow channel in direct fluid communication with the second chamber; wherein the expandable drive housing is expandable upon receiving the propellant from the propellant source and, upon expansion, causes forward axial movement of the syringe; and wherein the medicament delivery device is configured such that as the propellant is introduced into the expandable drive housing the propellant begins to pass directly through the narrow channel into the second chamber and causes forward axial movement of the stopper in the barrel to expel medicament contained in the first chamber through the open end, wherein the forward axial movement of the stopper in the barrel commences after the forward axial movement of the syringe.

2. The medicament delivery device of claim 1, wherein the expandable drive housing comprises a first part that is sealable to the propellant source, and a second part sealed to the barrel, wherein the second part is sealingly telescopically slidable relative to the first part to expand the expandable drive housing.

3. The medicament delivery device of claim 1, wherein an initial increase in pressure in the second chamber is at a rate that is less than 50%, 40%, 30%, 20%, 10%, 5% or 1% of a rate of initial increase of pressure in the expandable drive housing.

4. The medicament delivery device of claim 1, wherein the propellant source contains a liquefied gas.

5. The medicament delivery device of claim 1, wherein the propellant source contains one or more hydrofluoroalkanes ("HFAs").

6. The medicament delivery device of claim 1, wherein the propellant source contains one or more hydrofluoroolefins ("HFOs").

7. The medicament delivery device of claim 1, further comprising blocking means that are configured to at least partially restrict a flow rate of the propellant through the narrow channel, the blocking means being moveable between a first position and a second position relative to the narrow channel, wherein in the second position the blocking means permits a greater flow rate of the propellant through the narrow channel relative to the flow rate of the propellant through the narrow channel when the blocking means are in the first position.

8. The medicament delivery device of claim 7, wherein in the first position the blocking means substantially prevents flow of the propellant through the narrow channel.

9. The medicament delivery device of claim 7, wherein the narrow channel extends radially through a second part.

10. The medicament delivery device of claim 9, wherein the blocking means is axially moveable on the second part between the first position and the second position.

11. The medicament delivery device of claim 10, wherein the blocking means comprises a circumferential seal disposed on the second part.

12. The medicament delivery device of claim 10, wherein the blocking means further comprises a first abutment part and the expandable drive housing comprises a second abutment part, the first abutment part is configured to abut the second abutment part as the second abutment part moves axially relative to the first abutment part, and abutment of the first abutment part and the second abutment part causes axial movement of the blocking means from the first position to the second position.

13. The medicament delivery device of claim 12, wherein the second abutment part is provided on a first part of the expandable drive housing.

14. The medicament delivery device of claim 1, further comprising a needle in fluid communication with the open end.

15. The medicament delivery device of claim 14, wherein the syringe is moveable from a first axial position in which the needle is not exposed to a second axial position that is axially forward of the first axial position and in which the needle is configured to penetrate an injection site, wherein the syringe is in the second axial position prior to commencement of the forward axial movement of the stopper in the barrel.

16. The medicament delivery device of claim 15, wherein the medicament delivery device is configured such that a time period elapses between the syringe arriving at the second axial position and the commencement of the forward axial movement of the stopper in the barrel, the time period being at least one of the group consisting of 0.005, 0.01, 10 0.05 and 0.1 seconds.

17. The medicament delivery device of claim 15, further comprising an axially moveable needle shield that is moveable between a first shield position in which the needle is exposed when the syringe is in the second axial position and a second shield position in which the needle is not exposed when the syringe is in the second axial position.

18. The medicament delivery device of claim 17, wherein the needle shield is biased by biasing means towards the second shield position.

19. The medicament delivery device of claim 18, wherein the biasing means comprise a spring.

20. A medicament delivery device comprising: a syringe having a barrel with an open end, and a stopper axially moveable and received in the barrel separating a first chamber axially forward the stopper from a second chamber axially rearward the stopper; an expandable drive housing arranged to receive a propellant from a propellant source for providing a vapour pressure, the expandable drive housing having a channel in fluid communication with the second chamber; and blocking means configured to at least partially restrict a flow rate of the propellant through the channel, the blocking means being moveable between a first position and a second position relative to the channel such that in the second position the blocking means permits a greater flow rate of the propellant through the channel relative to the flow rate of the propellant through the channel when the blocking means are in the first position; wherein the expandable drive housing is expandable upon receiving the propellant from the propellant source and, upon expansion, causes forward axial movement of the syringe and movement of the blocking means from the first position to the second position; and wherein when the blocking means are in the second position the propellant introduced into the expandable drive housing is configured to pass through the channel into the second chamber and cause forward axial movement of the stopper in the barrel to expel medicament contained in the first chamber through the open end, wherein the forward axial movement of the stopper in the barrel commences after the forward axial movement of the syringe.

* * * * *